United States Patent
Tanji

(10) Patent No.: US 9,310,307 B2
(45) Date of Patent: Apr. 12, 2016

(54) METHOD AND DEVICE FOR PROCESSING DATA

(71) Applicant: CANON KABUSHIKI KAISHA, Tokyo (JP)

(72) Inventor: Koichi Tanji, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 15 days.

(21) Appl. No.: 14/290,769

(22) Filed: May 29, 2014

(65) Prior Publication Data

US 2014/0354988 A1 Dec. 4, 2014

(30) Foreign Application Priority Data

May 31, 2013 (JP) .................................. 2013-115683

(51) Int. Cl.
*G01J 3/44* (2006.01)
*G01N 21/65* (2006.01)
*G01J 3/28* (2006.01)

(52) U.S. Cl.
CPC . *G01N 21/65* (2013.01); *G01J 3/28* (2013.01); *G01J 3/44* (2013.01); *G01N 2021/655* (2013.01); *G01N 2201/129* (2013.01)

(58) Field of Classification Search
CPC .................. G01N 2201/129; G01N 2021/655; G01J 3/44
See application file for complete search history.

(56) References Cited

U.S. PATENT DOCUMENTS

| | | | | |
|---|---|---|---|---|
| 3,778,606 | A * | 12/1973 | Schmitt et al. ................ | 708/403 |
| 6,154,708 | A * | 11/2000 | Koashi ............................ | 702/40 |
| 6,732,064 | B1* | 5/2004 | Kadtke et al. ................. | 702/189 |
| 2006/0217938 | A1* | 9/2006 | Tracy et al. .................... | 702/189 |
| 2012/0016818 | A1* | 1/2012 | Hackett et al. ................. | 706/12 |

FOREIGN PATENT DOCUMENTS

JP 2011-174906 A 9/2011

* cited by examiner

*Primary Examiner* — Michael A Lyons
*Assistant Examiner* — Maurice Smith
(74) *Attorney, Agent, or Firm* — Canon U.S.A., Inc. IP Division

(57) ABSTRACT

High-speed data processing is achieved by measuring spectral data using a multivariate analysis. This is accomplished by a determining sampling intervals or sampling data to be used in the multivariate analysis, obtaining a spectral data group of the determined sampling intervals, and carrying out the multivariate analysis using the obtained spectral data group.

19 Claims, 5 Drawing Sheets

EQUAL INTERVALS

UNEQUAL INTERVALS

METHOD AND DEVICE FOR PROCESSING DATA

BACKGROUND

1. Field

Aspects of the present invention generally relate to methods and devices for processing measurement spectral data obtained by measuring biological tissue, and in particular relates to a method and a device for processing image data for a multivariate analysis.

2. Description of the Related Art

Conventionally, biological tissue has been observed with a microscope, and constituent substances or contained substances associated with the observed biological tissue have been visualized. For such visualization, mass spectrometry or Raman spectroscopy is employed. As a measurement spectrum, a mass spectrum, an ultraviolet, visible, or infrared optical spectrum, and so on are used. With such a measuring method, information on a spatial distribution of peak values in the measurement spectrum associated with the measured substance can be obtained, and thus a spatial distribution of the substance contained in the biological tissue associated with the measurement spectrum can be obtained.

With mass spectrometry, the time of flight of an electrically charged ion depends on mass m of the ion and an electric charge z. On the basis of the above, the ion can be identified, and a mass spectrum at each point on the sample can be obtained.

With Raman spectroscopy, a light source irradiates a substance with monochromatic laser light, and generated Raman scattered light is detected with a spectrometer or an interferometer so as to obtain a Raman spectrum. A difference between the frequency of the Raman scattered light and the frequency of the incident light (i.e., Raman shift) takes a value unique to the structure of the substance, and thus a Raman spectrum unique to the measured substance can be obtained.

To date, a multivariate analysis, in which intensity information of a broad wavelength band is handled as a variate, has been employed to analyze measurement spectral data. According to a principal component analysis (PCA) or an independent component analysis (ICA), which are types of the multivariate analysis, even with a complicated spectrum in which vibration spectra or band structures of components contained in a biological sample are superimposed on one another, the chemical state of the biological sample can be classified and measured. As an example, according to Japanese Patent Laid-Open No. 2011-174906, a PCA is carried out on an optical spectrum of each pixel to obtain a distribution of principal component scores, and thus morphologic information or composition of a biological sample is examined.

When a PCA is carried out, a sample variance-covariance matrix is obtained, and an eigenvalue and an eigenvector of the sample variance-covariance matrix are then obtained. A sample variance-covariance matrix, however, contains data having a size of a spectral number by a spectral number. Thus, when a spectral number used in an analysis is large or when a large number of pieces of image data are to be handled, the data amount increases, disadvantageously leading to an increased processing time.

SUMMARY OF THE INVENTION

Aspects of the present invention are generally directed to providing a method and a device that enable high-speed data processing by resampling a spectrum while retaining necessary information.

According to an aspect of the present invention, a data processing device is configured to process measurement spectral data by using a multivariate analysis. The data processing device includes a determination unit configured to, based on the measurement spectral data, determine sampling intervals or sampling data to be used in the multivariate analysis, a data group obtaining unit configured to obtain a spectral data group of the sampling intervals determined by the determination unit or a selected spectral data group, and a multivariate analysis unit configured to carry out the multivariate analysis by using the spectral data group obtained by the data group obtaining unit.

According to the present invention, a multivariate analysis, as represented by a PCA, can be carried out quickly by reducing a spectral number while retaining necessary information. Reducing the spectral number to be used in measurement in turn allows the measurement time to be reduced as well.

Further features of the present disclosure will become apparent from the following description of exemplary embodiments with reference to the attached drawings.

DESCRIPTION OF THE EMBODIMENTS

Hereinafter, an exemplary embodiment will be described in detail with reference to the flowcharts and the drawings. It should be noted that the specific example described below is merely an example and is not seen to be limiting. In the exemplary embodiment, a sample having a composition distribution within a space is measured, but additional exemplary embodiments are applicable to a result obtained through any method as long as such a method obtains measurement spectrum information associated with biological tissue or a substance distributed within biological tissue of a lesion, in correspondence with positional information on each point within the space and the position of each point.

Figure 4:
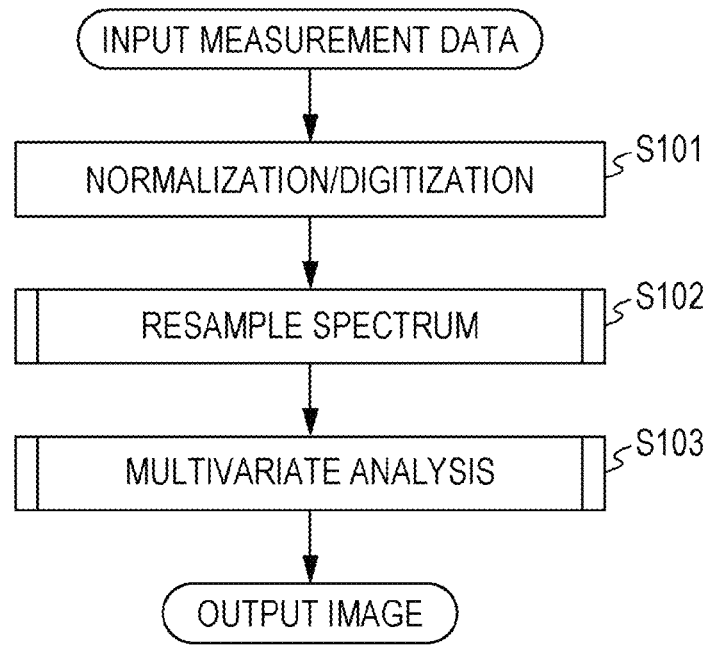
FIG. 4 is a flowchart of an overall processing method.

FIG. 4 illustrates a flowchart of an operation of a device according to an exemplary embodiment. Hereinafter, the exemplary embodiment will be described in the order of the flowchart while referring to the drawings.

In the exemplary embodiment, measurement data is first obtained.

Measurement data to be obtained is, for example, data on a measurement spectrum, and the measurement spectrum may be obtained through spectroscopy using an ultraviolet, visible, or infrared optical spectrum or through Raman spectroscopy using a Raman optical spectrum, or may be mass spectral data. A measurement spectrum obtained through spectroscopy or Raman spectroscopy has a measurement signal such as the one illustrated in FIG. 3B. In this case, signal intensities illustrated in FIG. 3C, which are obtained by discretizing the stated measurement signal, serve as signal intensity peaks.

Figure 3A:
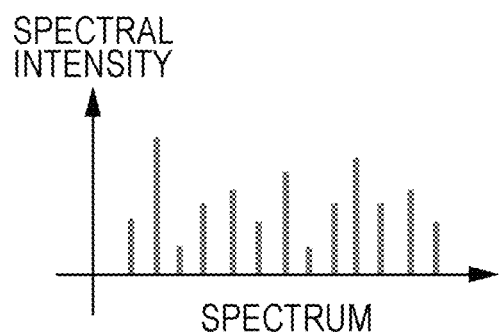
FIGS. 3A through 3C are conceptual diagrams of peak components in a spectrum.
Figure 3B:
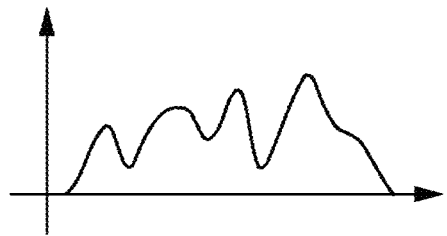
Figure 3B:
Figure 3C:
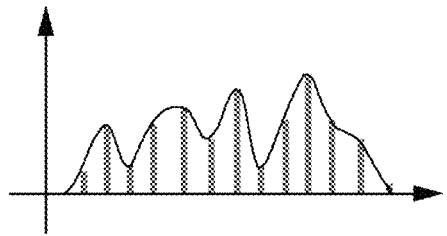

In a case in which mass spectral data such as the one illustrated in FIG. 3A is used, signal intensity peaks in the mass spectral data may be used.

Subsequently, in step S101 of FIG. 4, the data is normalized and digitized. Normalizing and digitizing processing of the data is carried out through an existing method.

Figure 2:
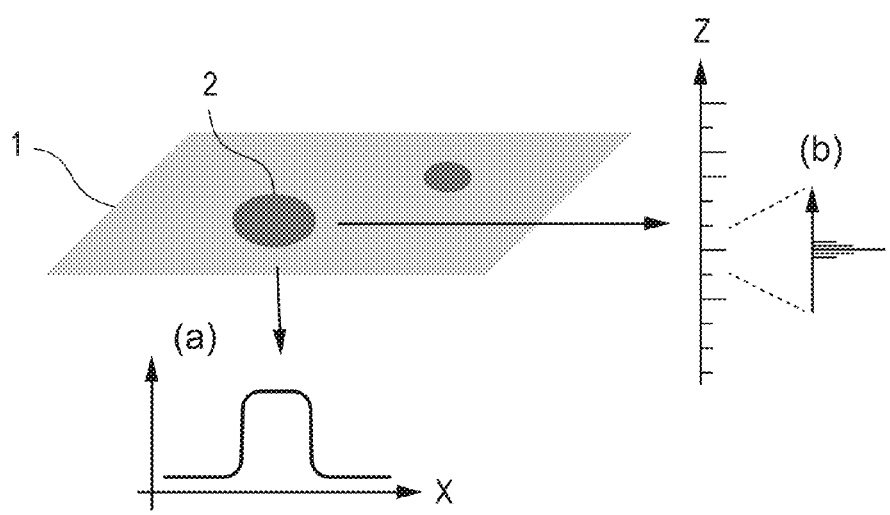
FIG. 2 schematically illustrates a spectral signal having an intensity distribution along a two-dimensional plane.

FIG. 2 schematically illustrates an intensity distribution of the measurement spectrum measured at each point in a space. For example, provided that the space in which a signal is obtained is a two-dimensional plane, information turns out to be three-dimensional data. Points in a three-dimensional space for generating the stated three-dimensional data are represented by coordinates (X, Y, A). Components X and Y correspond to coordinates on a two-dimensional space (XY plane) in which the measurement spectrum has been obtained and are indicated in section (a) of FIG. 2. A component A corresponds to a measurement spectral signal at each point on the XY plane and is indicated in section (b) of FIG. 2. Thus, the components X and Y contain the X-coordinate and the Y-coordinate, respectively, of a point at which the signal has been measured, and the component A contains a value of the measurement signal corresponding to the intensity of each peak component.

Data that can be used in the exemplary embodiment includes not only two-dimensional image data but also three-dimensional spatial data. In a case in which information on the component A in a Z direction relative to the XY plane can be obtained, the measurement data can be used as information on the component A relative to an XYZ space, or in other words, as four-dimensional information.

Although, for the sake of simplicity, data processing method in which two-dimensional information along the XY plane will be described in detail hereinafter, a processing method in which information on the Z direction is added can be implemented in a similar manner.

In step S102 of FIG. 4, the spectrum is resampled. Here, resampling is an operation for generating a new data group by sampling a previously obtained data array (data group) at a different sampling rate. Step S102 also includes an operation of selecting a spectrum to be used in a data analysis and generating a data group to be used in the data analysis.

Specifically, the stated resampling includes a determination operation in which sampling intervals to be used in a multivariate analysis is determined on the basis of the measurement spectral data and a data group obtaining operation in which a spectral data group of the determined sampling intervals is obtained. The stated resampling further includes a determination operation in which a spectrum to be used in the multivariate analysis is determined on the basis of the measurement spectral data and a data group obtaining operation in which a spectral data group selected by the determination unit is obtained.

Figure 5:
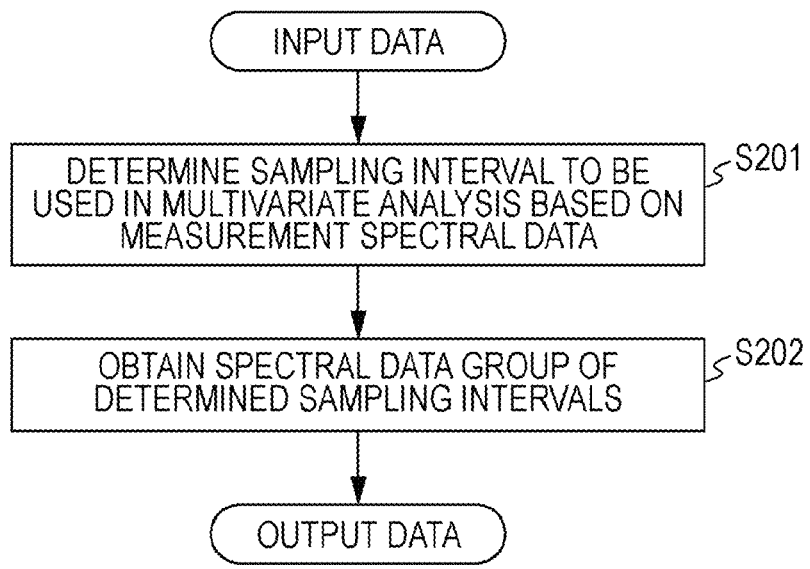
FIG. 5 is a flowchart of spectrum resampling.

FIG. 5 illustrates a flowchart of spectrum resampling. Hereinafter, the spectrum resampling will be described in the order of the flowchart while referring to the drawings.

Determination Operation of Determining Sampling Intervals Used in Multivariate Analysis on the Basis of Measurement Spectral Data In step S201 of FIG. 5, sampling intervals to be used in a multivariate analysis are determined.

The sampling intervals may be determined, for example, through a method that uses (1) a rate of change (second derivative) of a spectral distribution or a method that uses (2) intensity information in a frequency space. Furthermore, a spectrum to be resampled may be selected through a method that uses (3) the magnitude of the spectral intensity distribution or (4) the magnitude of the Mahalanobis distance. Hereinafter, each case will be described.

Figure 6A:
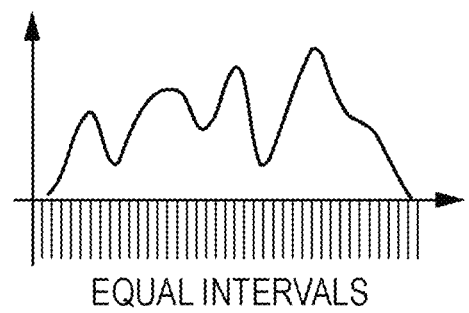
FIGS. 6A and 6B are schematic diagrams of spectrum resampling.
Figure 6A:
Figure 6B:
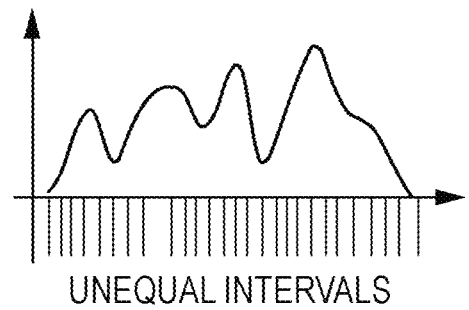

(1) Method that Uses a Rate of Change (Second Derivative) of a Spectral Distribution FIGS. 6A and 6B illustrate an example in which resampling intervals are determined on the basis of a rate of change of a spectral distribution. As compared with a case of sampling at equal intervals as illustrated in FIG. 6A, in a case illustrated in FIG. 6B, sampling intervals are condensed, or shortened, when the rate of change of the spectral distribution is large, and are made sparse, or lengthened, when the rate of change is small. Resampling at such sampling intervals makes it possible to reduce a spectral number to be used in a multivariate analysis carried out thereafter.

(2) Method that Uses Intensity Information in a Frequency Space

In a case in which intensity information in a frequency space is used, for example, after a spectrum is subjected to Fourier transform, a power spectrum is calculated, and a frequency to be used preferentially may be determined on the basis of the order of spectral intensities. By determining, in advance, a spectral number or an intensity threshold to be used, the sampling intervals can be calculated automatically.

(3) Method that Uses the Magnitude of the Spectral Intensity Distribution

In addition, when selecting a spectrum to be resampled, a spectrum may be selected with a focus on the magnitude of the spectral intensity distribution. For example, in the PCA, which is one of the methods for the multivariate analysis, an axis along which the distribution of a data projection component is maximized is selected as an axis along which the data is to be contracted. Thus, by preferentially selecting a spectral component with a greater distribution, a dominant spectral component in the result of the PCA can be selected.

(4) Method that Uses the Mahalanobis Distance

As another method for selecting a spectrum, the magnitude of the Mahalanobis distance may be used. The Mahalanobis distance is defined by a ratio between the between-groups variance and the within-group variance of spectral intensities corresponding to a plurality of measurement targets. If the Mahalanobis distance is large when the spectral intensities corresponding to the measurement targets are projected onto a multi-dimensional space, the components can be efficiently obtained and separated, for example, when the PCA is carried out. As a result, a dominant spectral component in the result of the PCA can be selected.

Data Group Obtaining Operation of Obtaining Spectral Data Group of Determined Sampling Intervals In step S202, a spectral data group of the sampling intervals determined in step S201 is obtained.

The data group may be obtained, for example, by averaging successive data points within a data array to generate a new data point, or in other word, by recalculating a spectral distribution.

Alternatively, measurement based on the determined sampling intervals may be newly carried out to obtain a data group. Specifically, previously obtained data may be subjected to spectrum resampling, and data can be newly obtained by using the obtained sampling intervals. Through this, the time it takes for the measurement can be reduced. As another alternative, the spectrum resampling can be carried out by simultaneously using data on a plurality of pixels around a pixel of interest.

Multivariate Analysis Operation of Carrying Out Multivariate Analysis by Using Obtained Spectral Data Group In step S103 of FIG. 4, a multivariate analysis is carried out by using the spectral data obtained in step S102. For the multivariate analysis, a PCA, in which high-dimensional data is compressed to lower-dimensional data, or an ICA, in which data is separated with a focus on a non-Gaussian statistical distribution, can be used.

For example, when the PCA is carried out, an eigenvalue and an eigenvector of a sample variance-covariance matrix having a size of a spectral number by a spectral number need to be calculated. Reducing the spectral number in step S102, however, makes it possible to greatly reduce the operation amount.

The present exemplary embodiment can be realized by a device that implements the specific example described above.

Figure 1:
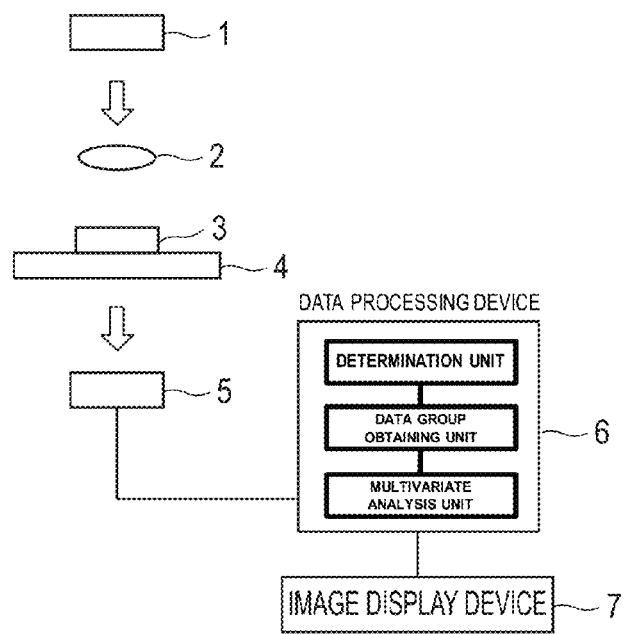
FIG. 1 schematically illustrates a sample information obtaining system.

FIG. 1 illustrates a configuration of a sample information obtaining system that includes a data processing device. The sample information obtaining system includes a light source 1 and an optical system 2. The sample information obtaining system measures a sample 3 disposed on a stage 4, and a detector 5 detects a signal. The light source 1, the optical system 2, the stage 4, and the detector 5 form a measuring unit for obtaining measurement spectral data of the sample 3.

A data processing device 6 carries out the above-described processing on an obtained signal, and an image display device 7 displays, on its screen, the result of the signal processing. In other words, the sample information obtaining system includes the measuring unit, the data processing device 6, and the image display device 7.

Exemplary Embodiment

First Exemplary Embodiment

Hereinafter, a first exemplary embodiment will be described. In the first exemplary embodiment, mouse pancreatic tissue is observed by using a microscope that utilizes stimulated Raman scattering. The power of a TiS laser used as a light source is 111 mW, and the intensity of a Yb fiber laser is 127 mW prior to being incident on an objective lens. The mouse pancreatic tissue serving as a sample is subjected to formalin fixation processing and sliced to a thickness of 100 micrometers. The tissue section is measured in a state in which the tissue section is embedded in glass along with a PBS buffer. The measurement area measures 160 micrometers on each side, and ten pieces of measurement data are integrated. The image data measures 500 pixels on each side, and the measurement time is 30 seconds.

On obtained spectral image data, XY coordinate information indicating a position of each measurement pixel and spectral information at each coordinate are recorded. For example, the spectral image data contains, as spectral data, information on a peak component associated with a component in the tissue contained in the sample.

Figure 7:
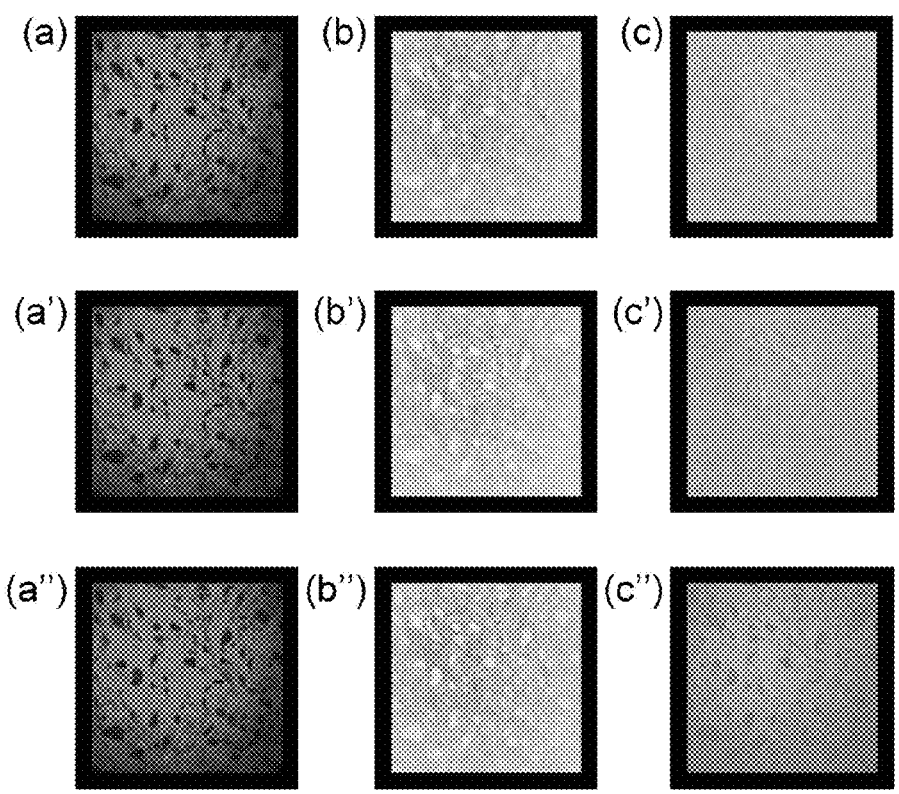
FIG. 7 illustrates an application effect of a first exemplary embodiment.

FIG. 7 illustrates, in section (a), a first principal component image, which is obtained by carrying out the PCA on the spectral image data obtained by measuring the mouse pancreatic tissue serving as the sample. FIG. 7 illustrates, in sections (b) and (c), a second principal component image and a third principal component image, respectively, obtained by carrying out the PCA in a similar manner.

In each of the cases, the measurement is carried out at spectral data sampling intervals of 1 kayser (1 cm$^{-1}$).

Subsequently, the spectral image data is subjected to spectrum resampling so as to be in proportion to the rate of change (second derivative) of the spectral distribution.

FIG. 7 illustrates, in section (a'), a first principal component image, which is obtained by carrying out the PCA on the resampled spectral image data.

FIG. 7 illustrates, in sections (b') and (c'), a second principal component image and a third principal component image, respectively, obtained by carrying out the PCA in a similar manner.

This resampling reduces the spectral number to approximately ⅔ and the time it takes for the PCA to approximately ½.

As can be seen when sections (a), (b), and (c) of FIG. 7 are compared with sections (a'), (b'), and (c') of FIG. 7, the principal component images obtained prior to and after the resampling do not change greatly.

On the contrary, in a case in which the sampling intervals are set to 1.5 kayser, principal component images illustrated in sections (a''), (b''), and (c'') of FIG. 7 are obtained. As can be seen when section (c) of FIG. 7 is compared with section (c'') of FIG. 7, if the sampling intervals are simply lengthened, a difference is generated between an obtained principal component image and an original principal component image.

In other words, it is indicated that the method of this exemplary embodiment enables the multivariate analysis to be carried out quickly while maintaining necessary information.

In addition, in this spectrum resampling, it is also possible to measure only a selected spectral component (referred to as premeasurement) and to obtain a first stage image. In this case, the entire spectra are measured (referred to as main measurement) after an approximate image is obtained through the premeasurement, and a final image is thus obtained. In addition, the entire wave numbers may be measured in a limited area of the entire image area in the premeasurement, and a necessary wave number may be selected on the basis of the spectral information of the stated area. In this case, while an area different from the area on which the premeasurement is carried out is measured in the main measurement, the measurement/analysis is carried out only for the wave number determined in the premeasurement, or in other words, the thinned wave number. Through this, the time it takes for the measurement and the analysis can be reduced.

The above-described exemplary embodiment(s) can be used as a tool that more effectively supports a multivariate analysis of spectral image data.

Other Embodiments

While exemplary embodiments have been described thus far, these exemplary embodiments are not seen to be limiting, and various modifications and changes can be made within the scope of the present disclosure.

Exemplary embodiments can be implemented, for example, in the form of a system, an apparatus, a method, a program, or a storage medium. The exemplary embodiments have been applied to the sample information obtaining system that includes the data processing device 6 and the image display device 7. The exemplary embodiments, however, may be applied to a system that is constituted by combinations of other devices or to an apparatus constituted by a single device.

In a system that is constituted by combinations of a plurality of devices to which the exemplary embodiments are applied, some or all of the devices may be interconnected through a network, such as the Internet. For example, obtained data may be transmitted to a server connected to a network, and the processing according to the exemplary embodiments may be carried out on the server. The obtained result may then be received from the server to display an image.

Furthermore, a software program according to the exemplary embodiments may be directly or remotely supplied to a system or an apparatus, and a computer of the system or the apparatus may load and execute the supplied program codes to realize the functions of the exemplary embodiments. In this case, the program to be supplied is a computer program corresponding to the flowcharts indicated in the exemplary embodiments. Thus, a program code itself installed in the computer to realize the functional processing of the exemplary embodiments also realizes the present disclosure.

In other words, the exemplary embodiments encompass a computer program that realizes the functional processing of the present disclosure. In that case, as long as being provided with the function of a program, an object code, a program executed by an interpreter, script data to be supplied to an operating system (OS) may be included.

A computer readable storage medium for supplying a computer program may, for example, be a hard disk, an optical disc, a magneto-optical disk, an MO, a CD-ROM, a CD-R, a CD-RW, or a magnetic tape. Furthermore, the storage medium may be a non-volatile memory card, a ROM, or a DVD (DVD-ROM, DVD-R).

Additionally, the program may be supplied by accessing a webpage through the Internet by using a browser on a client computer and downloading the computer program of the present disclosure from the webpage to a storage medium, such as a hard disk. In this case, the program to be downloaded may be in the form of a compressed file containing an automatic installation function. Furthermore, the present invention encompasses a WWW server that allows a plurality of users to download the program file that causes a computer to realize the functional processing of the present disclosure.

While the present disclosure has been described with reference to exemplary embodiments, it is to be understood that these exemplary embodiments are not seen to be limiting. The scope of the following claims is to be accorded the broadest interpretation so as to encompass all such modifications and equivalent structures and functions.

This application claims the benefit of Japanese Patent Application No. 2013-115683, filed May 31, 2013, which is hereby incorporated by reference herein in its entirety.

What is claimed is:

1. A data processing device configured to process measurement spectral data by using a multivariate analysis, the data processing device comprising:
    a determination unit configured to, based on the measurement spectral data, determine sampling intervals to be used in the multivariate analysis;
    a data group obtaining unit configured to obtain a spectral data group of the sampling intervals determined by the determination unit; and
    a multivariate analysis unit configured to carry out the multivariate analysis by using the spectral data group obtained by the data group obtaining unit,
    wherein the determination unit determines the sampling intervals based on one of a rate of change of a spectral distribution, intensity information in a frequency space, a magnitude of a spectral intensity distribution, or a magnitude of a Mahalanobis distance.

2. The data processing device according to claim 1,
    wherein the measurement spectral data is image data in which measurement spectral data is stored at each point along an XY plane.

3. The data processing device according to claim 1,
    wherein the determination unit determines the sampling intervals such that the sampling intervals are short when the rate of change of the spectral distribution is large and the sampling intervals are long when the rate of change of the spectral distribution is small.

4. The data processing device according to claim 1,
    wherein the determination unit calculates a power spectrum after subjecting the measurement spectral data to a Fourier transform and determines a frequency for sampling in an order of spectral intensities.

5. The data processing device according to claim 1,
    wherein the determination unit determines a spectrum to sample based on the magnitude of the spectral intensity distribution.

6. The data processing device according to claim 1,
    wherein the determination unit determines a spectrum to sample based on the magnitude of the Mahalanobis distance calculated from spectral intensities corresponding to a plurality of measurement targets.

7. The data processing device according to claim 1,
    wherein the data group obtaining unit measures a spectrum based on the sampling intervals determined by the determination unit.

8. The data processing device according to claim 1,
    wherein the measurement spectral data is data obtained through any one of an ultraviolet, visible, or infrared optical spectrum, a Raman optical spectrum, or a mass spectrum.

9. A sample information obtaining system, comprising:
    the data processing device according to claim 1; and
    a measuring unit configured to measure the measurement spectral data from a sample.

10. A data processing method for processing measurement spectral data by using a multivariate analysis, the data processing method comprising:
    determining, based on the measurement spectral data, sampling intervals to be used in the multivariate analysis;
    obtaining a spectral data group of the determined sampling intervals; and
    carrying out the multivariate analysis by using the obtained spectral data group,
    wherein determining the sampling intervals includes determining the sampling intervals based on one of a rate of change of a spectral distribution, intensity information in a frequency space, a magnitude of a spectral intensity distribution, or a magnitude of a Mahalanobis distance.

11. The data processing method according to claim 10,
    wherein the measurement spectral data is image data in which spectral data is stored at each point along an XY plane.

12. The data processing method according to claim 10,
    wherein determining the sampling intervals includes determining the sampling intervals such that the sampling intervals are short when the rate of change of the spectral distribution is large and the sampling intervals are long when the rate of change of the spectral distribution is small.

13. The data processing method according to claim 10,
    wherein determining the sampling intervals includes calculating a power spectrum after subjecting the measurement spectral data to a Fourier transform and determining a frequency for sampling in an order of spectral intensities.

14. The data processing method according to claim 10,
    wherein determining the spectral intervals includes determining a spectrum to sample based on the magnitude of the spectral intensity distribution.

15. The data processing method according to claim 10,
    wherein determining the spectral intervals includes determining a spectrum to sample based on the magnitude of the Mahalanobis distance calculated from spectral intensities corresponding to a plurality of measurement targets.

16. The data processing method according to claim 10, wherein obtaining the spectral data group includes measuring a signal based on the determined sampling intervals.

17. The data processing method according to claim 10, wherein a measurement spectrum of the measurement spectral data is one of an ultraviolet, visible, or infrared optical spectrum, a Raman optical spectrum, or a mass spectrum.

18. A computer readable storage medium storing a program that causes a computer to execute:
   determining, based on measurement spectral data, sampling intervals to be used in a multivariate analysis;
   obtaining a spectral data group of the determined sampling intervals; and
   carrying out a multivariate analysis by using the obtained spectral data group,
   wherein determining the sampling intervals includes determining the sampling intervals based on one of a rate of change of a spectral distribution, intensity information in a frequency space, a magnitude of a spectral intensity distribution, or a magnitude of a Mahalanobis distance.

19. A data processing device configured to process measurement spectral data by using a multivariate analysis, the data processing device comprising:
   determination code configured to, based on the measurement spectral data, determine sampling intervals to be used in the multivariate analysis;
   data group obtaining code configured to obtain a spectral data group of the sampling intervals determined by the determination code; and
   multivariate analysis code configured to carry out the multivariate analysis by using the spectral data group obtained by the data group obtaining code,
   wherein the determination code determines the sampling intervals based on one of a rate of change of a spectral distribution, intensity information in a frequency space, a magnitude of a spectral intensity distribution, or a magnitude of a Mahalanobis distance.

* * * * *